United States Patent [19]

McClatchie et al.

[11] 4,177,381
[45] Dec. 4, 1979

[54] GAS ANALYZER SAMPLE CELL

[75] Inventors: Edward A. McClatchie; Dean A. Watson, both of Berkeley; Irvin G. Burough, Walnut Creek, all of Calif.

[73] Assignee: Andros Incorporated, Berkeley, Calif.

[21] Appl. No.: 895,937

[22] Filed: Apr. 13, 1978

Related U.S. Application Data

[62] Division of Ser. No. 749,836, Dec. 13, 1976, Pat. No. 4,103,174, which is a division of Ser. No. 509,838, Sep. 27, 1974, Pat. No. 4,013,260.

[51] Int. Cl.² .................. G01J 1/00; G01N 1/10; G01N 21/24; G01N 21/26
[52] U.S. Cl. .................. 250/343; 250/576; 356/246; 356/410; 356/440
[58] Field of Search ............... 356/246, 410, 411, 440; 250/343, 576

[56] References Cited

U.S. PATENT DOCUMENTS 2,534,657  12/1950  Bray ........................ 250/343
3,207,026  9/1965  Churchill et al. ............ 250/576

*Primary Examiner*—Alfred E. Smith
*Assistant Examiner*—T. N. Grigsby
*Attorney, Agent, or Firm*—Fitch, Even & Tabin

[57] ABSTRACT

An improved gas analyzer for measuring the presence of one or more gaseous compounds in a gas sample. The gas analyzer has an infrared source stabilized against temperature variations by a radiation loading scheme in combination with a selected source environmental temperature sensitivity to provide a stable source temperature without a conventional temperature controller. A rotating interference filter assembly is disposed in the optical path. This assembly alternately totally blocks radiation, passes radiation in a wave length band which will not be absorbed by a random gas sample, and sequentially passes radiation in one or more additional bands which will be absorbed by one or more gases in the sample cell. The sample cell features a unique enclosed cell with infrared transparent windows which are substantially free of impingement of contaminants of the gas sample thereon. A unique detector provides protection against deterioration from moisture while allowing easy and inexpensive assembly. The system electronics eliminates sensitivities to background radiation, contamination of windows, etc., and provides a self test capability.

2 Claims, 17 Drawing Figures

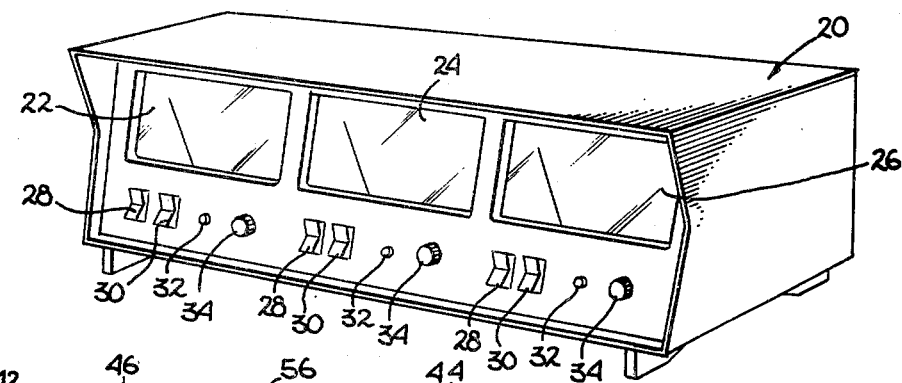
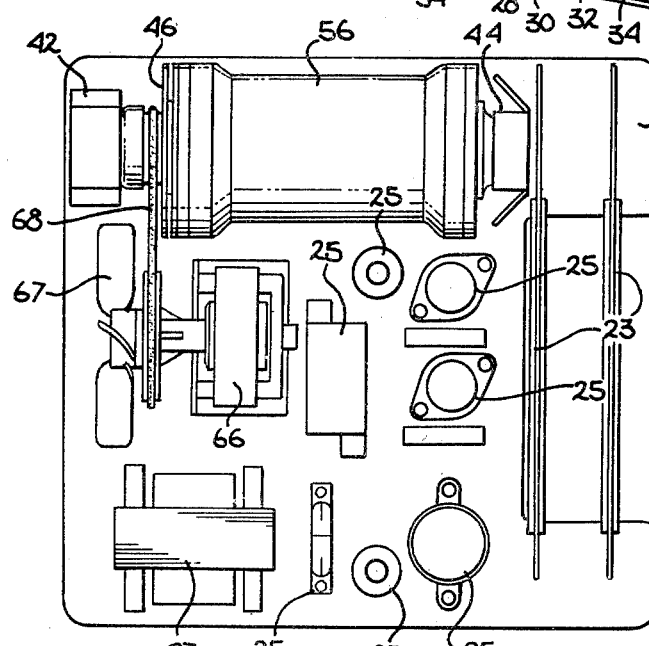
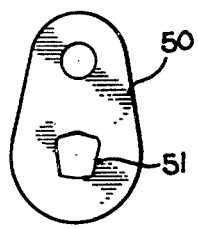

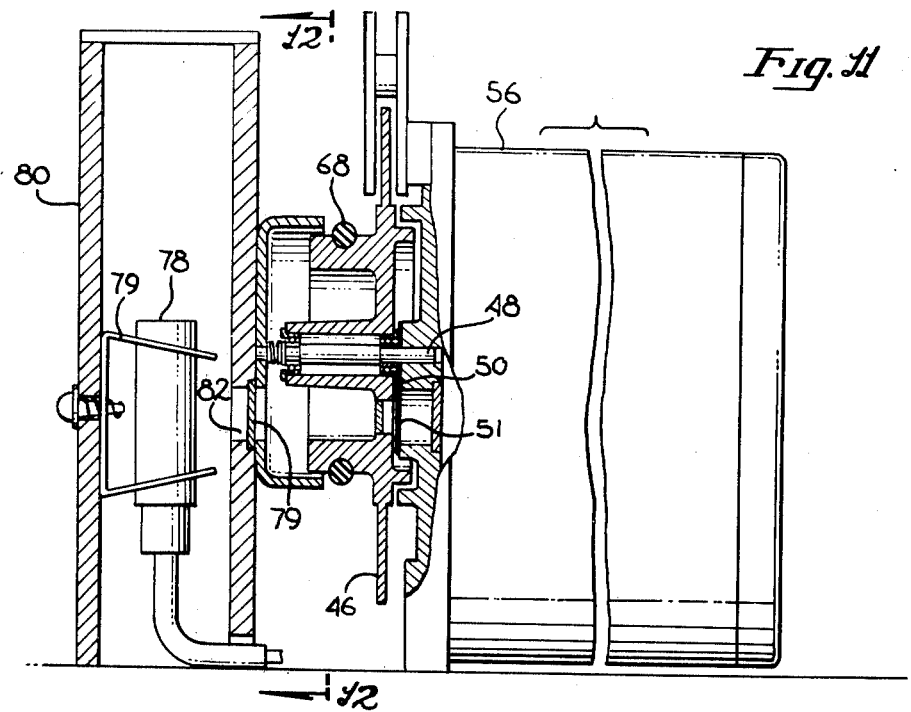
Fig. 11
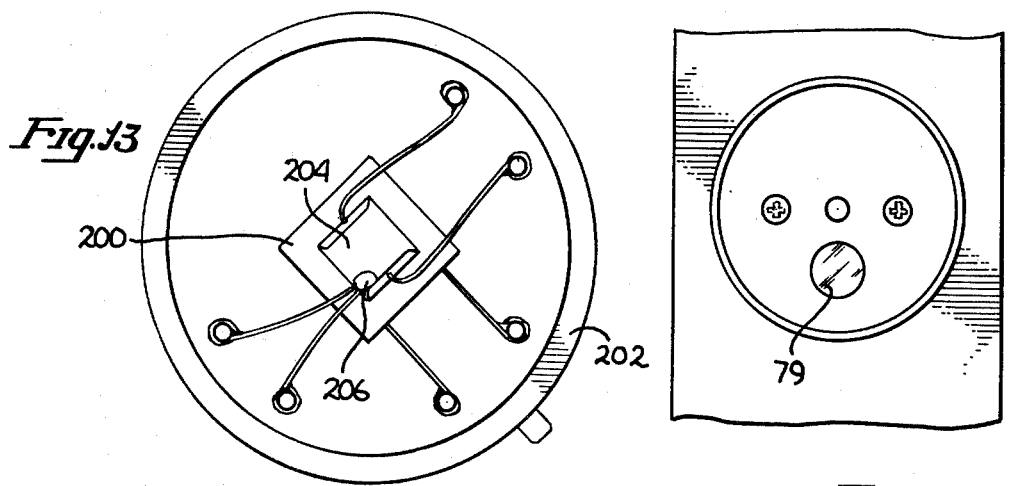
Fig. 13
Fig. 12
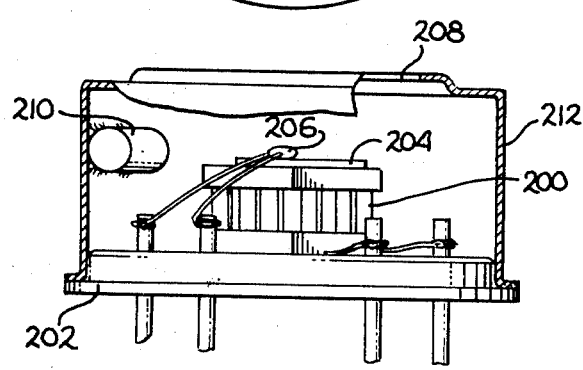
Fig. 14

GAS ANALYZER SAMPLE CELL

This is a division of application Ser. No. 749,836, filed Dec. 13, 1976, now U.S. Pat. No. 4,103,174 which was a division of Ser. No. 509,838, Sept. 27, 1974 now U.S. Pat. No. 4,013,260.

BACKGROUND OF THE INVENTION

1. Field of the Invention

The present invention relates to the field of non-dispersive infrared gas analyzers, and more particularly, to infrared non-dispersive gas analyzers intended for everyday use in measuring the presence of one or more gases in a random gas sample.

2. Prior Art

Non-dispersive infrared gas analyzers are generally known in the prior art. These analyzers utilize an infrared source, typically an electric heater, to provide infrared radiation through a gas sample for detection by a detector. Various schemes have been utilized by these devices for providing the desired signal utilizing both single and double optical path configurations.

The fact that various gases exhibit infrared absorption characteristics for specific wave lengths of infrared radiation is well known, and such phenomena is at least theoretically easily usable for the detection of specific gases in a random gas sample. However, there are a number of practical problems which detract from the stability and sensitivity of such devices. By way of example, contamination on the windows of the sample cell will alternate the radiation passing therethrough, which in most systems will be erroneously interpreted as the presence of the gas to be detected in the gas sample. Accordingly, many prior art systems required frequent renulling to cancel out the apparent zero offsets from this source. Furthermore, detector null shifts and IR source temperature changes would similarly provide a rather unstable zero output of these devices.

To minimize the IR source temperature shift, some prior art IR non-dispersive gas analyzers utilize a temperature controlled mounting for the IR source. Thus, the IR source is itself mounted on a base or platform which was heated to some fixed temperature above the normally expected ambient, and maintained at the temperature by some form of temperature control system. This system might be merely a mechanical thermostat for turning the power on and off, in which case, the temperature of the IR source will tend to cycle with the thermostat. Proportional temperature controllers are also used, which avoid this temperature cycling problem. However, such controllers are expensive since the amount of power being controlled may be as high as 1000 watts or more.

Prior art sample cells for retaining the gas sample in the optical path are generally closed cells having an inlet port adjacent at one end and an outlet port adjacent at the other end, and with infrared transparent windows at each end thereof. The sample gas flow through this type of sample cell is such as to encourage direct impingement of oils, particulate matter and other contaminates onto at least one of the infrared transparent windows, thereby tending to contaminate the window. This produces zero shift if the contaminant is a material to which the analyzer is sensitive and cuts down its transmissibility at a reasonably rapid rate resulting in deterioration of performance and ultimately cessation of proper operation. Minimizing window contamination in such sample cells is accomplished by rather fine gas stream filtration, resulting in higher maintenance effort and cost, and greater hangup due to the filter itself. To solve this problem, one prior art sample cell utilizes an air curtain in place of the transparent windows, wherein a flow of air passes each end of the sample cell, tending to contain the sample within the bounds determined by the air curtain. Thus, the window contamination problem is eliminated by elimination of the window itself. However, the air curtain system requires a separate air pump as well as other structure in order to accomplish the task, and tends to define a varying sample length thereby providing some uncertainty in the analyzer output. Furthermore, such sample cells are not enclosed, so that other components of the analyzer will be exposed to some contamination by the gas sample.

Prior art detectors typically are photoconductive devices mounted on a thermoelectric cooler with a thermister also mounted on the cooler. The entire assembly is mounted in a transistor can or other package with an infrared transparent window over the photoconductor. Such devices in cooperation with a temperature controller controlling the thermoelectric cooler in response to the thermister output are highly accurate and reliable devices provided the integrity of the hermetic seal on the can is preserved. If, however, only minor leaks occur, the inclusion of any moisture into the can usually causes rapid deterioration of the photoconductor, thereby providing a very unstable analyzer output and ultimately resulting in the total failure of the analyzer.

Prior art electronics for use with non-dispersive infrared gas analyzers are generally adapted to measure a detector signal and to provide an output in a manner consistent with the principal of operation of the analyzer. These electronic circuits have not provided a self test feature, etc., and typically required a large number of components to achieve the required task. The net result is that prior art analyzers tend to require zero adjustment, and periodic servicing and cleaning to maintain the devices in a satisfactory operating condition.

BRIEF DESCRIPTION OF THE DRAWINGS

FIG. 1a is a perspective view of one embodiment of the present invention.

FIG. 1b is a top view of the present invention system with the case removed.

FIG. 2 is a schematic representation of the system of the present invention.

FIG. 11 is a partial cross-section of the IR source and filter wheel.

FIG. 12 is a view taken along lines 12—12 of FIG. 11 showing the face view of the IR source.

FIG. 13 is a top view of the detector assembly.

FIG. 14 is a partial cross-sectional view of the detector assembly.

FIG. 15 is a face view of the aperture plate defining the aperture for the optical system.

DETAILED DESCRIPTION OF THE INVENTION

Figure 3:
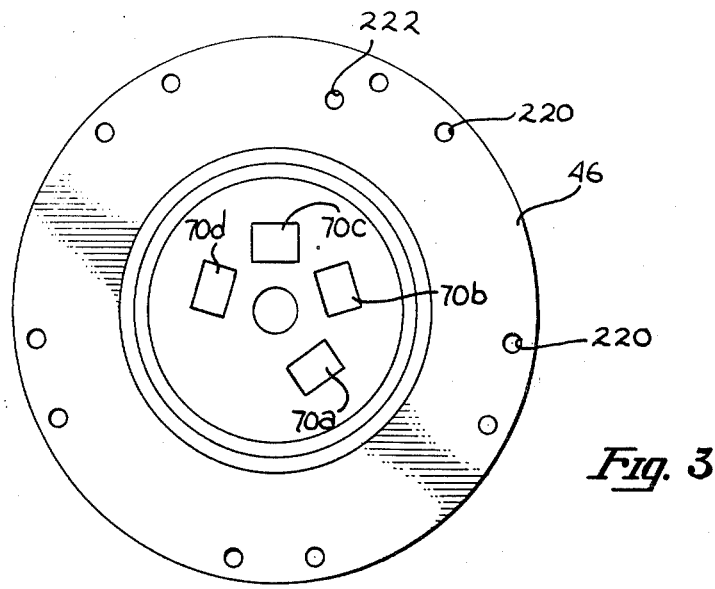
FIG. 3 is a face view of the rotating filter wheel.

First referring to FIG. 1a, a perspective view of the gas analyzer of the present invention may be seen. The gas analyzer of the preferred embodiment described herein is mounted in a case 20 having three meters 22, 24 and 26 on the front thereof. Each of the meters has associated therewith a first switch 28 to select a high and a low range for the meters (using conventional meter scaling techniques), a second switch 30 for providing a self test and calibration feature later described in detail, and a span (gain) adjustment 32 and a zero adjustment 34 for adjusting the range and zero position of the respective meter, typically based upon some standard reference test used for calibration. The first meter is to indicate the amount of hydrocarbons in the gas sample, typically in parts per million. The second meter is to indicate the percentage of $CO_2$ in the sample and the third meter is to indicate the percentage of CO in the sample. Thus, in the specific embodiment described herein, tests for three constituents of the gas sample may be conducted at the same time. It should be noted however, that present requirements for automobile exhaust analyzers, one possible use for the preferred embodiment, only provide for the measurement of hydrocarbons and carbon monoxide, and of course the present invention may be readily used for such tests with or without the carbon dioxide sensing provided in the embodiment disclosed herein. Also, for such testing it is common to provide a pumping means to assure reasonable sample gas flow through the sample cell, and to further provide some form of filter for filtering particulate matter from the gas sample before the sample is provided to the sample cell in the gas analyzer. Such pump and filter are both well known in the prior art, and in some instances, depending upon the use of the analyzer, not required, and therefore are not described in detail herein. The present invention does have a specific advantage also in not being sensitive to sample flow rates.

Now referring to FIG. 1b, a top view of the main gas analyzer assembly of the gas analyzer of FIG. 1a may be seen. The analyzer is constructed on a frame member 21 with the electronic circuit therefor mounted on a printed circuit boards 23 extending vertically from a printed circuit board connectors at the rear of the frame 21. Components 25 such as power transistors, large capacitors, wiring juction boxes, etc., which because the heat dissipation and/or their physical size are not easily mounted on the printed circuit board 23, are mounted directly to the frame 21. Similarly, a main power transformer 27 is also mounted to the frame. Other major components visible in the figure are a motor 66 with a cooling fan 67, a drive belt 68 extending between the motor and a rotating filter assembly 46, an infrared source 42, a sample cell 56 (with inlets and outlets being oriented vertically below the sample cell) and detector assembly 44.

Now referring to FIG. 2, a block diagram of the system of the present invention may be seen. A power supply 40 provides power to an infrared source 42. The source 42 is located at one end of an infrared optical path which terminates at the other end at detector 44. In line in this optical path is a rotating filter 46, rotating about an axis 48 parallel to but displaced from the optical path, an aperture 51 before the first of two infrared transparent windows 52 and 54 at the end of a sample cell 56, and a collector 58 for receiving and reflecting the infrared radiation passing through window 54 onto the detector 44. Processing electronics 60 are provided for amplification and to synchronize the detector signal from detector 44 with the position of the rotating filter 46 by a signal received from the filter position sensors 61 and 62, and to provide a plurality of outputs to drive the indicators 22, 24 and 26. In the preferred embodiment, the rotating filter 46 is driven by an approximately 3450 RPM non synchronous motor 66 through a drive belt 68 so as to rotate at a speed of approximately 6,000 RPM.

The rotating filter itself is better schematically illustrated in FIG. 3, which schematically illustrates the face of the rotating filter of the preferred embodiment. The rotating filter is essentially separated into five segments of seventy-two degrees each, with four of the five segments containing filter elements 70A through 70D, and with the fifth angular segment being occupied by a solid portion of the wheel. As will be subsequently shown, the filter elements 70A through 70D are each to pass narrow bands of infrared radiation, each having different band centers at predetermined wave lengths to provide three measuring signals and one reference signal. The fifth angular segment of the wheel, having no such filter in the preferred embodiment, is utilized to block the source radiation from the sample cell so that the detector signal may be used to indicate combined effects such as background radiation, detector null, electronics offset, etc. Accordingly, the present invention will be described with reference to a specific embodiment for measuring the concentration of three specific gases in the gas sample, it being understood that a less or greater number of infrared absorbing gas components may be measured by making simple and obvious modifications of the specific embodiment disclosed herein. In particular, the specific embodiment disclosed herein is designed to measure concentrations of hydrocarbons, carbon monoxide and carbon dioxide present in the sample cell 56, and for greater specificity of the description of a specific embodiment, will be so described, it being understood that such description is exemplary only and not by way of limitation of the invention.

Figure 4:
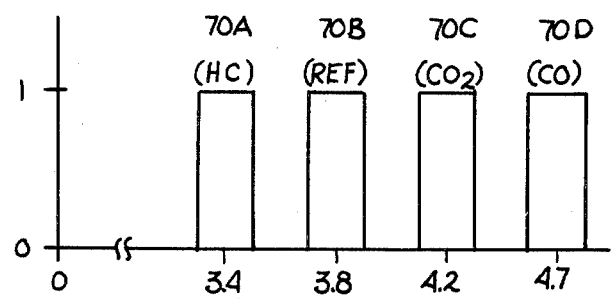
FIG. 4 is a graphic representation of the ideal band pass characteristics of the interference filters in the filter wheel of FIG. 3.

The specific embodiment of the present invention described in detail herein is primarily intended for use as an automobile engine exhaust gas analyzer. Accordingly, the hydrocarbons desired to be measured generally have their greatest infrared absorption in a wave length region centered around 3.4 microns. Carbon dioxide is centered around 4.2 microns, whereas carbon monoxide is generally centered around 4.7 microns (approximate values). For reasons which will subsequently become more apparent, it is desirable to have the reference filter centered as close to the gases being sensed as possible without significant overlap with any of the gases. Accordingly, in the preferred embodiment, a reference filter is designed to have an IR pass band centered at 3.8 microns. The ideal situation is illustrated in FIG. 4, wherein the ideal band pass characteristics of each of the four filters is illustrated. In practice, however, the ideal sharp cutoff cannot be achieved. Accordingly, unless the filters are very carefully designed and controlled, the band pass characteristics of the filters may overlap and pass significant amplitudes of radiation in the undesired regions. By way of example, the reference filter is intended to provide a measure of the intensity of the infrared radiation in the optical path independent of the presence or absence of a gas sample in the sample cell. Thus, the band width and the center of the band for the reference filter are desired to be in an infrared non-responsive region for typical gas samples to be tested, as ideally illustrated in FIG. 4. However, the reference filter band pass, if not carefully controlled, may not be centered on the desired wave length and/or may more gradually trail off so as to pass significant amounts of radiation which may be absorbed by the hydrocarbons and/or the carbon dioxide in the gas sample. In such event, the reference signal would not be a true reference signal, but would also be somewhat responsive to the presence of a gas sample. A similar result is achieved to the extent that the absorption characteristics of the gases to be detected may overlap and/or extend into the wave length band utilized for the reference signal.

The basic theory of operation of the system is as follows: The detector signal measured when the reference filter is aligned in the optical path provides a measure of the basic sensitivity of the system to infrared radiation in general. That is, it provides a measure of the strength of the radiation of the IR source, the attenuation of the radiation by [non-spectral] contamination and the like on the infrared transparent windows in the sample cell, and further provides a measure of the effectiveness of the collector and the sensitivity of the detector as well as the gain of the processing electronics. Each of the other filters provide radiation which ideally can only be absorbed, if at all, by the presence of the specific gas to be detected through the use of that filter. Of course, contamination on the windows, variations in the IR source, radiation detector, etc. will also vary the signal received, which sensitivity may be minimized by the use of the reference signal which is similarly affected.

Figure 5:
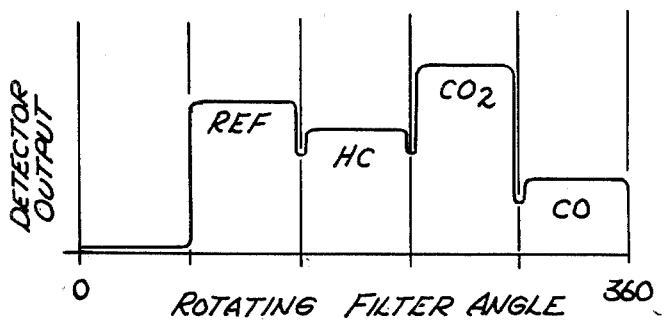
FIG. 5 is a graphical representation of the detector output versus filter wheel angle.

In practice, for an evacuated sample cell, or in the alternative for a sample cell containing gases other than the gases to be detected, the detector signal versus rotating filter angular position might appear as shown in FIG. 5. Thus, because of such effects as different optical characteristics of the filters, and source radiation and detector wave length sensitivities, the four signals received will be of different amplitudes. These signals could be equalized optically, by controlling the aperture of each reference filter, or electronically by sampling the smaller signals for a longer time with a circuit sensitive to the time amplitude characteristics rather than mere amplitude or amplitude-fixed time product characteristic of the sensing, by way of example. This is difficult, however, because such mechanical changes involve costly mechanical complexities and time consuming adjustment, and the fixed sample time circuits are by far the easiest to fabricate and use. Another method of equalizing the signals would be to add an appropriate bias voltage to each of the signals, by way of example, to bring all of the signals up to a predetermined level. This, however, would still result in a system which was sensitive to optical characteristics changes, since if by way of example, the optical windows collected contamination so as to drop all signal strengths by twenty percent, the bias voltage would not drop accordingly, and the four signals would no longer be equal when the sample cell was free of the gas to be detected. This would result in various output signals in a condition when no output signals should be present. In the preferred embodiment, the detector signals for each of the four filters are measured for a predetermined angle of the filter wheel, utilizing a system having a different gain for each of the sensed signals predetermined to equalize the signals when none of the gases to be measured are present in the sample cell. Thus, variations in intensity of the radiation in the optical system caused by contamination on the sample cell windows, etc. will generally vary all signals in proportion so that the four signals will track each other with a high degree of accuracy.

In furtherance of the foregoing objective, it should be noted that there is a certain amount of background radiation present in any such system. This is radiation which will be incident upon the detector even when the infrared radiation source is off, or blocked from radiating into the sample cell by the solid portion of the rotating filter assembly. Other signals are also present which are functionally equivalent to the background radiation, such as possible null output of the detector, input offsets in the electronics, etc. These signals typically do not vary with variations in source intensity, IR window transmissability, etc., and accordingly should be removed from all signals before the gain adjustment is made to equalize the outputs.

Figure 6:
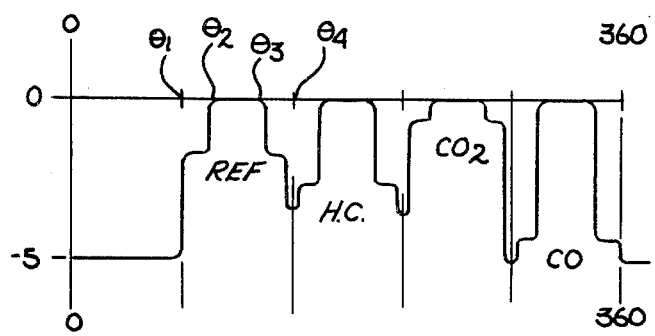
FIG. 6 is a graphical representation of a conditioned detector signal versus filter wheel angle after the base line and gain changes have been made in the respective signals.

In the preferred embodiment, and in a manner which will subsequently be described in detail, the system is provided with a basic gain which is switched during each measurement phase so that the desired gain for that measurement is achieved, and an averaging circuit is utilized to provide an output which is responsive to the average detector signal throughout the sensing time. By averaging the signal in this manner over the time required for the rotation of the filter wheel through a predetermined arc (10 degrees in the preferred embodiment) the effect of noise is minimized (whereas point sampling would be very noise-sensitive). Also as will be subsequently be seen in greater detail, the standard gain is lower than the gain used for sensing each of the desired signals, with the gain being switched upward by an adjustable amount during each sensing phase. Further, when the solid portion of the rotating filter assembly is disposed in the optical path, the detector signal is sensed and used to establish a reference level, in the preferred embodiment selected to be minus 5 volts, with the gain adjustment then being made to amplify the detector signals to zero volts for the four other signals (assuming the sample cell to be empty). Accordingly, the preamp output appears as shown in FIG. 6. It will be noted that for the first approximately 72 degrees the source radiation is blanked by the solid portion of the rotating filters and during a part of this time the minus 5 volt reference level is electronically established. At a filter angle of approximately $\theta_1$ (e.g. approximately 72 degrees), the reference filter comes into view in the optical path, phasing out again at the angle $\theta_4$ as the hydrocarbon filter comes into view. Of course, there is some filter angle range required for any filter to totally pass in or pass out of the optical path, and in the preferred embodiment, sensing of the detector signal (and changing the gain) is done over a filter angle range between $\theta_2$ and $\theta_3$ purposely made narrower than the range $\theta_1$ to $\theta_4$ to avoid filter changes during sensing. This provides a steady signal (except for normal ripple) during sensing, with the shape of the aperture 51 (FIG. 15) being chosen in conjunction with the shape of the interference filters to maximize the optical window area sensing time product for a given interference filter area.

Having now described the basic operation of the system, the various individual components and subassemblies thereof shall be described. Many of these components and subassemblies are unique, and offer greater advantages over known prior art devices, either as part of the overall present invention system, or in other systems requiring such components and/or subassemblies.

The IR Source

The infrared radiation source is a very important component in infrared non-dispersive gas analyzers, particularly in the analyzer of the type described in detail herein, as the source must have controlled radiation characteristics throughout a significant wavelength range. Though the magnitude of the radiation could be allowed to increase or decrease, it must do so in a fixed proportion throughout this range, a characteristic not common in black-body radiators, as the shape of the intensity v. wave length curve changes substantially as the temperature of the radiator changes. Accordingly, it is important that the temperature of the source be maintained as constant as possible. In prior art equipment it was common to put the infrared source in a temperature-controlled environment, typically elevated in temperature through the use of a temperature controller so that a fixed voltage on an infrared source would result in a fixed temperature difference between the elevated reference temperature and the source, thereby giving a constant source temperature. This, however, requires considerable warm-up time and tends to add to the complexity and cost of the equipment, and any hysterisis in the temperature controller will cause a commensurate dither in the meter readings.

Figure 8:
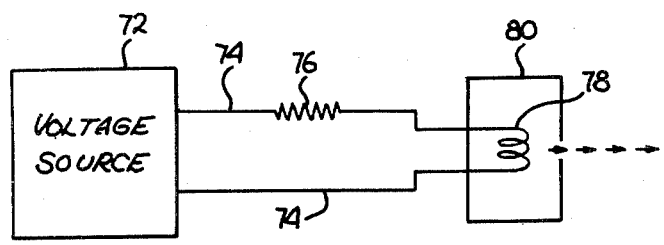
FIG. 8 is a block diagram of the radiation loaded IR source.

In the preferred embodiment of the present invention, a system is utilized to maintain the IR source at a substantially constant temperature regardless of environmental temperature changes without utilizing any system of source mount temperature control. The system for doing this is illustrated in FIGS. 8, 11 and 12 and is comprised of four basic elements. These are a voltage regulator (voltage-controlled power supply) 72, lead wires 74, including a significant temperature sensitive resistance 76 (illustrated in lumped parameter form in FIG. 8 but in practice merely being the resistance of the lead wires themselves) an infrared source 78, on mount 79, and a source enclosure 80 having an opening 82 (with IR transparent window 79) to allow radiation from the source 78 to precede along the optical path.

There are three primary sources of heat loss from the infrared source 78. These are conduction, convection, and radiation. Both conduction and convection tend to be dependent upon the temperature differential between the IR source and the environment (and of course are dependent upon the geometry of the components, etc.). On the other hand, radiation is dependent upon the emissivity and temperature to the fourth power. If the emissivity of the IR source is very low, the loss by radiation will be minor in comparison to the loss by conduction and convection and accordingly, the temperature of the IR source will tend to be fixed differential above the temperature of the entire instrument. Accordingly, if the room temperature increases by 30 degrees, the temperature of the IR source will also tend to increase by 30 degrees. On the other hand, if convection and conduction may be minimized and the emissivities may be made large (approaching unity) the primary energy loss from the IR source will be by radiation. Since for this type of equipment the IR source should have a temperature somewhere in the area of 1000 degrees K., the IR source is approximately three times as hot as the background, or the temperature ratio to the fourth power is approximately 81 to 1. Accordingly, the IR source will be radiating energy 81 times faster than the background is radiating energy to the source. The net result is that the temperature of the IR source is rendered quite insensitive to variations in temperature of the source enclosure 80. This mechanism also results in the source temperature being less sensitive to its input voltage as well, than it would be with weaker radiative ballasting. Accordingly, one aspect of the source stabilizing system is to provide an IR radiator 78 with as high an emissivity as possible and to provide the structure in view of the source with a high emissivity also to prevent reflection back to the source. While emissivities of 1.0 would be desired, these of course cannot be achieved, though an emissivity (for infrared radiation) of at least 0.7 should be achieved, and preferably emissivities of approximately 0.85 should be used. Surfaces painted black and/or oxidized surfaces and/or deliberately roughened surfaces will provide the desired emissivities.

The effect from these high emissivities may be referred to as radiation loading, this loading tending to provide a background temperature insensitive IR source. There will, of course, be some sensitivity to the background or instrument temperature due to conduction and convection, and for that matter, a small amount of radiation back to the source from the background which may be roughly linearized over a reasonable range. To substantially eliminate this sensitivity, the voltage source 72 may be made to have a slight temperature sensitivity itself so that when background temperature goes up the output of the voltage source decreases by a compensating amount. It has been found, however, that the amount of voltage swing required over a reasonable temperature range is quite low, and lead wires 74 of a preselected length, size and positive temperature coefficient of resistivity will achieve the desired result with a high degree of accuracy. Accordingly, with a conventional voltage source, a conventional IR source modified to have a high emissivity, and control of the emissivity of the background in view by the IR source coupled with the selection of the lead characterisitics provides a high degree of stability of the IR source temperature without special heaters or temperature controllers. The present invention source provides source control without using the heaters which in the prior art sometimes required more than 1000 watts and require a longer warm-up time than the present invention.

The Sample Cell

Two types of sample cells have been utilized in prior art analyzers. The first and the most conventional is a tube-like structure having infrared transparent windows at each end thereof, with an inlet adjacent one end and an outlet adjacent the othe end. The gas to be measured is delivered to the sample cell through the inlet, travelling the length of the sample cell and being removed therefrom through the outlet. This type of cell essentially provides a closed sample system with a fixed length sample (e.g., determined by the size of the sample cell). However, it has the disadvantage that the flow stream is directed toward one of the transparent windows in the sample cell and particulate matter and oil vapors which have not been filtered out of the sample will tend to impinge on the window, detracting from the transmissibility of the window and from the operation of the system over a period of time. Accordingly, system performance will decrease with time at a rate dependent upon the filters used and the frequency with which they are cleaned.

Another type of sample cell eliminates the IR transparent windows and in place thereof, an air-curtain or air-stream is provided to generally contain the sample within the sample cell. This system avoids contamination of the windows by eliminating the windows, though since the sample cell is not sealed some contamination may accumulate in other parts of the system and in addition, the sample length will tend to vary thereby detracting from the accuracy of the system and providing some instability in particular reading. This system also generally requires a separate pump for the air-curtain and accordingly is more expensive than simple IR transparent windows. In the present invention, a novel sample cell is used which approaches the advantages of the air-curtain arrangement while maintaining the accuracy, stability and approaching the simplicity of the simpler prior art sample cells.

Figure 10:
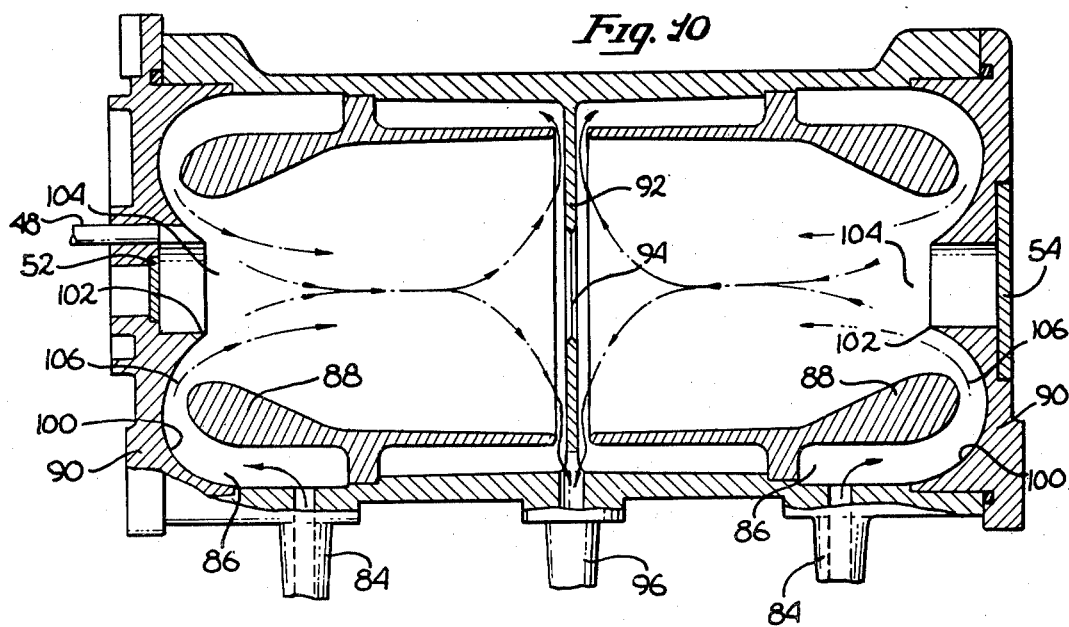
FIG. 10 is a cross-section of the sample cell.

A cross-section of the sample cell 56 of the present invention may be seen in FIG. 10. The cell is characterized by first and second inlet ports 84 which pass the sample into cylindrical plenum-like areas 86 to distribute the sample around the periphery of the cell. The flow proceeds between the inner member 88 and the endcap 90 to be injected into the central area of the sample cell with a substantial velocity component toward the central member 92. The central member 92 has an opening 94 therein to accommodate the optical system, though the member 92 tends to divide the sample cell into two half sections with the sample being caught on each side thereof for passage out through the exhaust port 96. It will be noted that member 88 has a smooth, air-foil like cross-section whereas the outer flow path 100 terminates with a reasonably sharp edge 102 to force separation of the flow from the wall at that point. Accordingly, the flow is as shown in FIG. 10, with the region 104 acting substantially as a stagnation area, that is a region of relatively quiet and undisturbed air. Also in this embodiment, the flow path cross-sectional area between member 88 and surface 100 decreases from the plenum region 86 to a minimum in region 106 located after the major portion of the flow path turn has been made. This assures a decreasing pressure along the flow path while the turn is being made, thereby avoiding possible boundary layer separation to minimize turbulence in the sample cell (which is more likely to disturb the stagnation area of stagnation plug at each end adjacent the infrared transparent windows 52 and 54.) The advantages of this sample cell, which are achieved principally by providing the means for injecting the sample from each end of the cell in the direction generally inward toward the central region of the cell, area that a fixed sample length is achieved in an enclosed system (the stagnation plug 104 will be composed of sample gas, though the rate of exchange of the gas in region 104 with the remainder of the sample in the sample cell will not be high). At the same time, no flow is directed toward any of the transparent windows. Accordingly, any contamination in the sample not previously removed by filters will not impinge and tend to adhere to the windows. Further, not only is the direct impingement on the windows eliminated, but the stagnation plug minimizes the circulation in the vicinity of the windows consistent with the requirements of providing a fixed length sample so that the condensation of condensable vapors onto the windows will also be minimized. Accordingly, a relatively low cost sample cell is provided, having the advantages of an enclosed sample system with minimum cleaning and maintenance being required because of the unique structure thereof.

The Detector

Typical IR radiation detectors are relatively temperature sensitive and therefore it is common practice to temperature stabilize such detectors to provide the desired stability in the wave length v. detector sensitivity curve. Accordingly, devices are available on the market which comprise an IR detector and a thermistor mounted on a thermoelectric cooler, all of which is mounted on a transistor can having infrared transparent window over the IR detector. IR detectors such as PbSe detectors are typically very moisture sensitive, deteriorating rapidly upon the condensation of any significant moisture from the surrounding environment. Accordingly, the package must be hermetically sealed to avoid unacceptable degradation with time caused by leaks allowing humid air to penetrate the enclosure and condense onto the detector at the reduced temperature. (Heating to a stabilized elevated temperature minimized the moisture problem, but results in a lower detector sensitivity and increased noise in the detector signal.)

The prior art detectors, together with a temperature controller of conventional design controlling the thermoelectric cooler based upon the thermistor output have been utilizied for the present invention. Failures in the package seal, however, generally result in a nonoperative detector after a period of time.

The modification of this prior art detector shown in FIGS. 13 and 14, results in a lower cost detector, having an improved reliability and higher manufacturing yield. In particular, the modification uses a conventional thermoelectric cooler 200 on an integrated circuit base 202, with the detector 204 being mounted to the top of the cooler. In the preferred embodiment, a lead selenide (PbSe) detector is used. The detector 204 is mounted just under the IR transparent window 208, which in the preferred embodiment is a sapphire window. Also mounted on the top of the thermoelectric cooler in the preferred embodiment on the detector itself, is a thermistor 206 to measure the temperature of that portion of the cooler and thus the temperature of the detector 204. In addition, the detector of the present invention has fastened therein a dessicant 210. In the preferred embodiment, the dessicant is in the form of a molecular sieve having the characteristic of absorbing relatively large quantities of moisture. The particular molecular sieve which has been used is the type 5A, manufactured by Linde Molecular Sieves, a subsidiary of Union Carbide Corp., 270 Park Ave., N.Y., N.Y., though other sieves, such as their types 3A and 4A could also be used. One or more pellets of the molecular sieve may be cemented or otherwise fastened either to the base 202 or to the cover 212 so as to be exposed to the internal environment of the transistor can. The presence of the dessicant greatly reduces the hermeticity requirement for the package sealing, and greatly prolongs the life of the detector even in the presence of small leaks. Finally, the sapphire window 208 may be cemented in place with epoxy and the cover fastened to the base in any coventional manner.

The Synchronizing System

Figure 9:
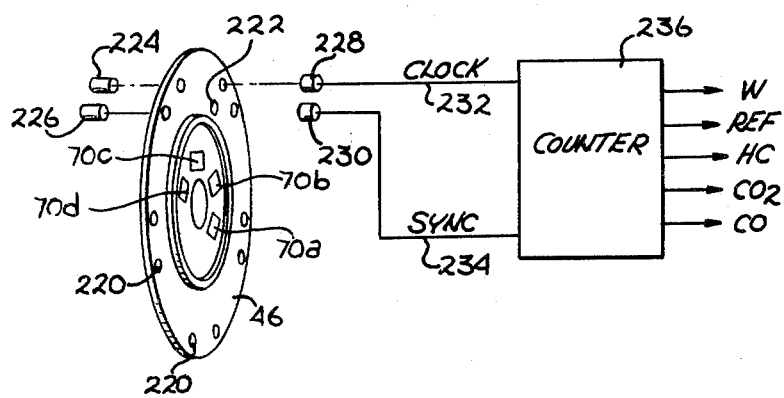
FIG. 9 is a schematic representation of the synchronizing system.

The synchronizing system is best described with respect to FIGS. 3 and 9. The interference filters 70A through 70D are disposed in four sections of a pentagon pattern in an inner portion of the rotating filter wheel 46. Adjacent the outer periphery of the wheel are plurality of holes 220. In particular, ten holes 220 disposed in groups of two around the periphery of the wheel. The angular arc between the two holes in each group is equal to the angular arc between $\theta_2$ and $\theta_3$ in FIG. 6. In addition, there is one additional hole 222 at a different (slightly smaller) radius. Accordingly, in FIG. 9 light-admitting diodes 224 and 226 disposed on one side of the wheel in conjunction with photo sensors 228 and 230 on the other side of the wheel will detect the passage of each of the respective holes between the light-admitting diode and the associated detector. Detector 228 is used to sense the passage of holes 220 and thus in single rotation of the rotating filter wheel ten pulses will be detected, referred to as the clock pulses. On the other hand, detecter 230 will provide one pulse per revolution, referred to as the sync pulse.

Figure 7:
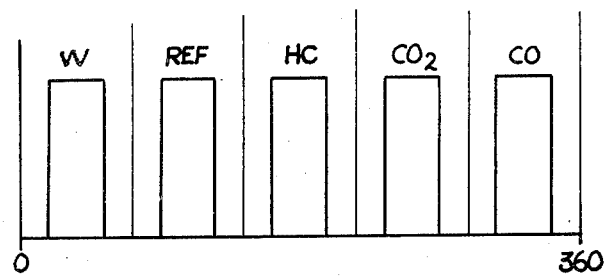
FIG. 7 is a graphical representation of the five switching signals versus filter wheel angle.

Both the clock pulse on line 232 and the sync pulse on line 234 are provided to a ring counter 236 which counts through the clock pulses, resetting (initializing) on the occurrence of the sync pulse so as to assure the proper beginning of the count in each rotation of the filter wheel. The ring counter 236 provides the basic sequencing for the electronic system and is intended to provide a first pulse W (of width $\theta_3-\theta_2$) during the passage of the solid portion of the reference filter 78, a third pulse HC during the passage of the hydrocarbon interference filter, etc. providing five such pulses. These pulses are illustrated in FIG. 7, and in the conventional ring counter may be achieved by taking every other output of the counter.

The Electronics

Figure 16:
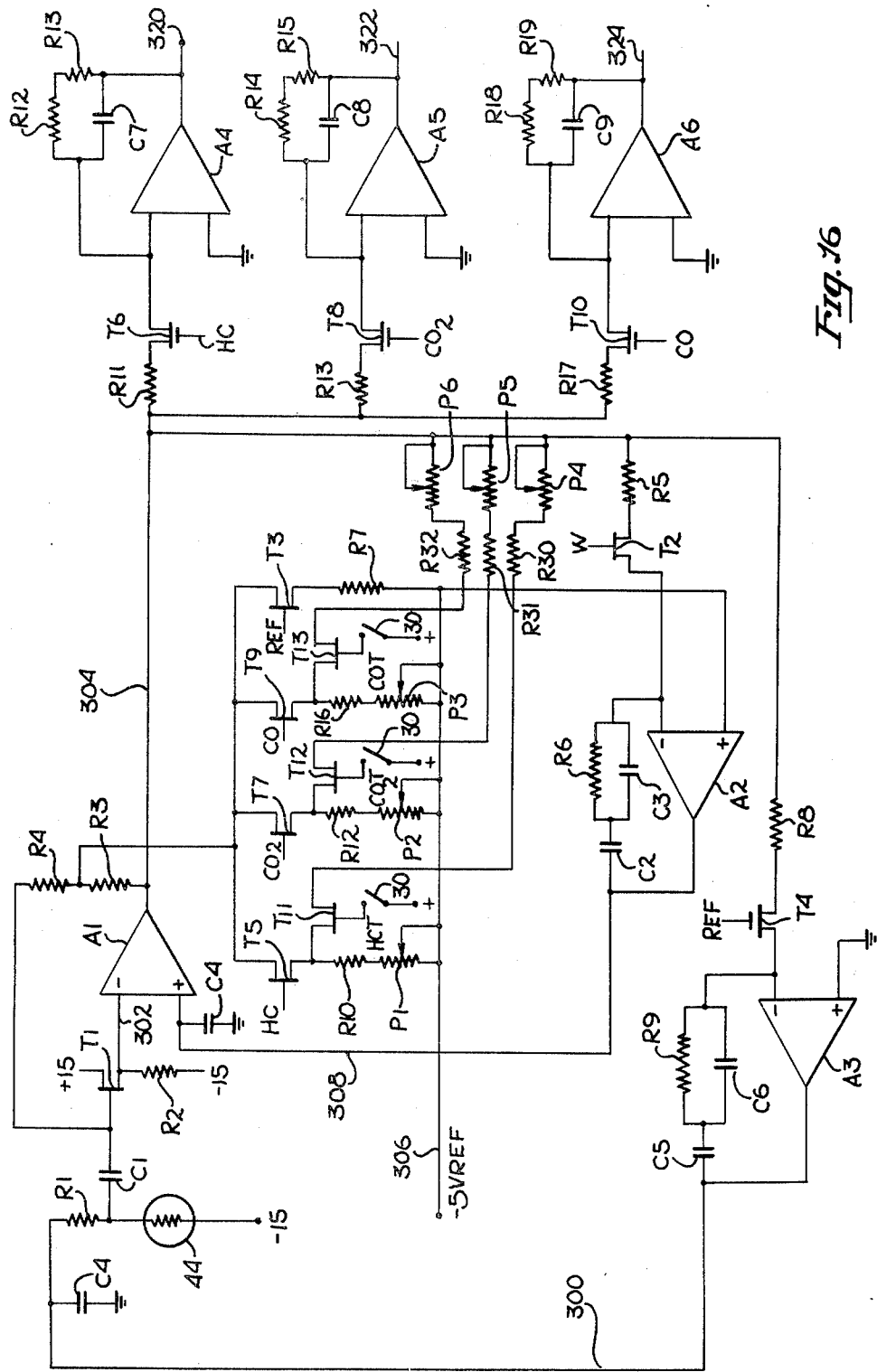
FIG. 16 is a circuit diagram for the electronics for the present invention.

The electronics circuit of the present invention may be seen in FIG. 16. In this figure, only the primary functional components are illustrated, it being understood the various amplifiers may also have compensating circuits, nulling circuits and the like as may be required for the individual type being used and that other circuit elements such as filters, voltage limiters, etc. may be used, at various points in the circuit, all such omitted items being well known in the art. The detector 44, a photoconductor, has one lead thereof connected to a minus 15 volt reference supply, with the other lead coupled through resistor R1 to line 300 and through capacitor C1 to low noise source follower T1, connected in turn directly to amplifier A1. Capacitor C1 couples the signal to field effect device T1, with the source of device T1 being coupled through resistor R2 to a minus 15 volt supply and coupled through line 302 to the negative input of amplifier A1. The output of amplifier A1 one line 304 is fed back through resistors R3 and R4 and the apparent source impedance of the signal applied to the gate device T1 as determined by the detector resistance and the resistance of resistor R1.

When the solid portion of the filter wheel is aligned with the optical path, the ring counter will provide an output signal W thereby turning on field effect device T2. This couples the negative input of amplifier A2 to the output of amplifier A1 on line 304 through resistor R5. The positive input of amplifier A2 is coupled to the minus 5 volt reference voltage on line 306, with the output being coupled back to the negative input through capacitors C2 and C3 and resistor R6. Accordingly, amplifier A2 servos the voltage on line 308 to a value such that the output on line 304 in this condition is minus 5 volts. The combination of capacitor C2 and C3 and resistor R6 provides for some averaging of the signals to avoid the noise problems which would be encountered by true point sampling, and provides a holding capability when the pulse W applied to the gate of device T2 is removed and further provides the servo loop filter which ensures the dynamic stability of the servo loop. Accordingly, upon the occurrence of the pulse W, line 308 is driven to a voltage such that the output of amplifier A1 is minus 5 volts, with the voltage on line 308 essentially holding at the level, in part through the action of capacitor C4, until being encouraged toward a newly corrected voltage upon the next rotation of the filter wheel on the next occurrence of the pulse W. Following the pulse W, and when the reference filter is aligned with the optical system, the pulse REF occurs. The occurrence of this pulse does two things. First, it turns on field effect device switch T3, coupling resistor R7 between the minus 5 volt reference on line 306 and the junction between resistors R3 and R4. This immediately reduces the feedback of amplifier A1, switching the amplifier to a higher gain condition, specifically to a gain selected so as to always provide a reference output voltage on line 304 which is higher than the uncorrected signals which will be achieved with the three remaining filters. It is this gain switching which increases the amplitude of the reference signal between the angles $\theta_2$ and $\theta_3$ as shown in FIG. 6. Secondly, the occurrence of the pulse REF turns on field effect device T4, coupling the output of amplifier A1 on line 304 through resistor R8 to the negative input of amplifier A3. Since the positive input of this amplifier is coupled to the ground, the amplifier amplifies the difference between the voltage then occurring on line 304 and ground to increase or decrease the voltage applied to the detector circuit comprised of resistor R1 and the detector 44, with capacitors, C4, C5 and C6 together with resistor R9 providing the desired averaging, holding and desired loop dynamic capability. Thus, it may be seen that a function of the circuit comprised in part of amplifier A2 is to provide a minus 5 volt base line when only background radiation is being sensed, and the function of the circuit comprised in part of amplifier A3 is to provide a gain such that the reference signal has 5 volt amplitude, e.g., minus 5 volt base line to 0 volt peak references.

It is to be noted that while the rotating filter could be between the sample cell and the detector, it is best located in the position shown in FIG. 2 as that allows the cancellation of the background radiation in the sample cell when the solid portion of the rotating filter is aligned in the optical path. Also, to ensure maximum utilization of the area of each interference filter and still avoid any signal measurement during transition from one filter to another and further to eliminate transmission of radiation via reflection from the cell walls, aperture plate 50 (FIGS. 2, 11 and 15) having a specially shaped aperture 51 is used.

After the occurrence of the REF pulse, the HC pulse indicating the alignment of the hydrocarbon reference filter in the optical system will occur. This turns on field effect device T5 coupling resistor R10 and potentiometer P1 between line 306 and the junction between resistors R3 and R4. As before, this cuts the feedback for amplifier A1, jumping the gain so that, assuming there are no hydrocarbons in the sample cell, the hydrocarbon signal of the detector will be amplified to have a 5 volt peak ranging from minus 5 to 0 as also indicated in FIG. 6. Potentiometer P1 provides an adjustment for this gain to allow for filter differences, etc. from system to system. Once the system has been adjusted, that is, the position of potentiometer P1 set so that the signal appearing on line 304 is 0 when there are no hydrocarbons in the sample cell, the presence of any hydrocarbons in the sample cell thereafter will result in the absorption of some of the infrared radiation passed through the sample cell by the hydrocarbon interference filter, thereby reducing the voltage on line 304 from 0 to some negative value depending upon the amount of hydrocarbons present, thereby providing the desired sensed output. This signal is coupled through resistor R11 and field effect device T6, also turned on by the pulse HC, to provide the input to amplifier A4 which again provides the averaging capabilities through resistors R12 and R13 and capacitor C7.

It will be apparent that the remaining circuits operative on the $CO_2$ and the CO pulse provide the sensing of carbon dioxide and carbon monoxide respectively in the same manner as heretofore described with respect to the hydrocarbons. Accordingly, the presence of the $CO_2$ pulse turns on field effect devices T7 and T8, jumping the gain through register R12 and potentiometer P2 and providing averaging through registers R13, R14 and R15 and capacitor C8. The CO signal turns on devices T9 and T10, jumping the gain through resistor R16 and potentiometer P3 and providing the averaging through resistors R17, R18 and R19, capacitor C9 and amplifier A6. Accordingly, the output voltages on lines 320, 322 and 324 provide an accurate measure of the hydrocarbons, carbon dioxide and carbon monoxide present in the sample cell (the scaling of the outputs may be accomplished by any conventional means, not shown, such as the simple expedient of adding a resistance as required in series with a meter or other indicating device).

The present invention has a self-test feature which enables an operator to quite quickly determine whether the system is operating properly or not. This is achieved by allowing an operator to himself provide a step gain change to the amplifier A1. By way of example, to test the hydrocarbon detector channel, the first of switches 30 (FIGS. 1 and 16) may be depressed, thereby turning on field effect device T11. This couples resistor R30 and potentiometer P4 between the output of amplifier A1 and the junction between the resistors R3 and R4 when device T5 is on, thereby decreasing the amplifier gain by increasing the feedback resistance when device T5 is on by an amount adjustable within limits by the potentiometer P4. The effect is to provide a self-test for substantially the entire hydrocarbon channel. When the sample cell does not contain any hydrocarbons, the output at terminal 320 will be zero before the hydrocarbon test swicth is depressed. When the hydrocarbon test switch is depressed, the output on terminal 320 should increase to a preset level. This could only occur if the source, optical transmission system, and detector are operating properly and if the automatic gain control circuit is properly functioning, as the measurement of the reference signal amplitude must be accurate and the detection of the absence of hydrocarbons in the sample cell must also be accurate. Furthermore, the synchronizing system must be operating properly or the turning on of device T11 will not effect the amplifier output. Furthermore, the output detector comprised of amplifier A4 and device T6 must be properly operating, or the output on terminal 320 will not change in the appropriate amount. Further, the base line circuit is effectively tested since the step change in output is an indication that the initial zero output was not caused by a short or open or other malfunction but was instead caused by the operation of the circuit associated with amplifier A2 to establish the minus 5 volt reference base line. Similar self-test capabilities are provided by devices T12 and T13 in conjunction with resistors R31 and R32 and potentiometers P5 and P6 for the other two channels.

There has been described herein a specific embodiment of the present invention gas analyzer, that specific embodiment having been described with respect to the detection of the presence of hydrocarbons, carbon monoxide and carbon dioxide. This specific description, however, is for purposes of specificity of one particular embodiment, and the usefulness of the present invention is by no means limited to this specific embodiment or the detection of the three gases or any of them described herein. By way of example, automobile exhaust gas analyzers presently only need to measure the hydrocarbon content and the carbon monoxide content in the engine exhaust. Accordingly, one embodiment of the present invention has been fabricated having the basic structure described herein but omitting the carbon dioxide interference filter and associated processing channel in the electronics system.

It is to be understood also that each of the various components or subassemblies making up the present invention system has been described with respect to the preferred form for accomplishing the various functions of that part of the system. However, various components of the system and the system itself will function properly and provide most of the advantages of the present invention if one or more of the unique components or subassemblies of the present invention is replaced with the equivalent components or subassemblies of conventional design. Thus, while the novel sample cell detector assembly and processing electronics of the present invention will provide the desired result even when used with a prior art infrared source, the inclusion of the present invention source with radiation loading reduces the power required for a stable source temperature from that required by most prior art sources, and provides faster warm up to a stable operating condition. Similarly, the sample cell of the present invention may be replaced with a conventional sample cell, though more frequent cleaning and maintenance will be required.

By way of further example, the infrared source and rotating filter assembly utilizing the interference filters may be replaced with a different system, such as a rotating system having one or more chambers each filled with the respective gas to be detected. Utilizing an infrared source disposed outside of the main optical path, the gases in the chambers may be sequentially stimulated in the IR source, and conveyed to the main optical path while fluorescing to provide the desired radiation into the sample cell. Said radiation would be comprised of the specific desired bands to provide maximum sensitivity of the system. Similarly, fluorescent phenomena of certain gases may be used to achieve similar results using stationary chambers and a rotating optical chopper wheel.

It should be noted further, that the relative disposition of the various components of the present invention along the optical path may be varied, although the specific arrangement disclosed herein, particularly with respect to FIG. 2, has been found preferable. In particular, it is most desirable to locate the rotating filter assembly at the source end of the sample cell rather than at the detector end, since such location allows the cancellation of the effect of background radiation originating from within the sample cell. Thus, when the solid portion of the rotating filter is aligned in the optical path, the establishment of the minus 5 volt reference not only cancels amplifier nulls, etc., but further cancels any detector signal which results from background radiation within the sample cell. This would not be true if the rotating filter were placed between the sample cell and the detector, as the solid portion of the wheel would block not only the source radiation, but the background radiation as well during this phase of the rotation of the filter.

Thus, it may be seen from the foregoing, that while the present invention has been disclosed and described with respect to a specific embodiment thereof, it will be understood by those skilled in the art that various changes in form and detail may be made therein without departing from the spirit and scope of the invention.

We claim:

1. A sample cell for an infrared gas analyzer comprising:
    an enclosure for a gas sample;
    first and second windows in said enclosure, one of said windows being adjacent each end of said enclosure, said windows being substantially transparent to infrared radiation so as to define an infrared radiation path through said sample cell;
    inlet means adjacent each end of the said enclosure for providing a gas sample to the interior of said cell adjacent each end thereof, outlet means between said inlet means for removing a gas sample from said cell,
    flow control means adjacent each end of said enclosure for receiving a gas sample from the respective inlet means and establishing flows having substantial components toward said outlet means and having a substantial component in the radial inward direction, thereby creating a form of stagnation plug inwardly adjacent each of said windows,
    and a central member extending transversely in the interior of said sample cell substantially midway between the ends thereof and having an opening accommodating the radiation path, said central member being spaced from said outlet means to allow removal of gas from both sides of said central member.

2. The cell of claim 1 wherein the surface defining said inlet means adjacent each window has a sharp discontinuity to induce fluid flow separation at said discontinuity.